(12) United States Patent
Zhang (10) Patent No.: US 11,291,550 B2
(45) Date of Patent: Apr. 5, 2022

(54) ARTICULAR FOSSA PROSTHESIS AND ARTICULAR PROSTHESIS WITH ARTICULAR FOSSA PROSTHESIS

(71) Applicant: Beijing AK Medical Co., Ltd., Beijing (CN)

(72) Inventor: Weiping Zhang, Beijing (CN)

(73) Assignee: Beijing AK Medical Co., Ltd., Beijing (CN)

( * ) Notice: Subject to any disclaimer, the term of this patent is extended or adjusted under 35 U.S.C. 154(b) by 0 days.

(21) Appl. No.: 16/957,124

(22) PCT Filed: Apr. 4, 2019

(86) PCT No.: PCT/CN2019/081495
§ 371 (c)(1),
(2) Date: Jun. 23, 2020

(87) PCT Pub. No.: WO2020/155376
PCT Pub. Date: Aug. 6, 2020

(65) Prior Publication Data
US 2021/0361438 A1    Nov. 25, 2021

(30) Foreign Application Priority Data
Feb. 1, 2019  (CN) .......................... 201910105283.9

(51) Int. Cl.
*A61F 2/34*    (2006.01)
*A61F 2/30*    (2006.01)

(52) U.S. Cl.
CPC ...... *A61F 2/34* (2013.01); *A61F 2002/30383* (2013.01); *A61F 2002/30649* (2013.01);
(Continued)

(58) Field of Classification Search
CPC .............. A61F 2/34; A61F 2002/30383; A61F 2002/30649; A61F 2002/30673;
(Continued)

(56) References Cited

U.S. PATENT DOCUMENTS 3,903,549 A * 9/1975 Deyerle .................... A61F 2/34
623/22.36
4,159,544 A * 7/1979 Termanini ................. A61F 2/32
623/22.14
(Continued)

FOREIGN PATENT DOCUMENTS

CN         1671333 A      9/2005
CN       203861388 U     10/2014
(Continued)

OTHER PUBLICATIONS

The extended European search report for the corresponding EP patent application No. 19912506.3, dated Nov. 30, 2021.

*Primary Examiner* — Yashita Sharma
*Assistant Examiner* — Melissa A Hoban
(74) *Attorney, Agent, or Firm* — Gang Yu (57) ABSTRACT

The disclosure provides an articular fossa prosthesis and an articular prosthesis with the articular fossa prosthesis. An outer cup of the articular fossa prosthesis is disposed in a target skeleton, a lining is disposed in the outer cup, an articular head structure may be movably disposed in the lining, a first communicating passage communicated with an articular capsule is disposed on the outer cup, a second communicating passage communicated with the articular capsule is disposed on the lining, and the first communicating passage is communicated with the second communicating passage to guide a synovial fluid to a contact surface between the lining and the articular head structure.

19 Claims, 4 Drawing Sheets

(52) U.S. Cl.
CPC .............. *A61F 2002/30673* (2013.01); *A61F 2002/3443* (2013.01); *A61F 2002/3469* (2013.01)

(58) Field of Classification Search
CPC ...... A61F 2002/3443; A61F 2002/3469; A61F 2002/3408; A61F 2002/3208
See application file for complete search history.

(56) References Cited

U.S. PATENT DOCUMENTS

| | | | | |
|---|---|---|---|---|
| 5,092,897 | A * | 3/1992 | Forte | A61F 2/4637 623/22.18 |
| 5,282,864 | A * | 2/1994 | Noiles | A61F 2/34 623/23.43 |
| 5,443,519 | A * | 8/1995 | Averill | A61F 2/34 623/22.22 |
| 5,480,448 | A * | 1/1996 | Mikhail | A61F 2/4637 623/22.24 |
| 5,549,700 | A * | 8/1996 | Graham | A61F 2/3609 623/22.14 |
| 5,571,198 | A * | 11/1996 | Drucker | A61F 2/30744 623/22.34 |
| 5,641,323 | A * | 6/1997 | Caldarise | A61F 2/30 623/22.18 |
| 5,769,093 | A * | 6/1998 | Bays | A61F 2/30742 128/898 |
| 5,916,269 | A * | 6/1999 | Serbousek | A61F 2/34 623/22.24 |
| 5,976,144 | A * | 11/1999 | Fishbein | A61B 17/1684 606/70 |
| 6,063,123 | A * | 5/2000 | Burrows | A61F 2/4637 623/22.21 |
| 6,231,612 | B1 * | 5/2001 | Balay | A61F 2/30771 623/22.31 |
| 6,358,282 | B1 * | 3/2002 | Wymann | A61F 2/4637 623/22.28 |
| 6,454,809 | B1 * | 9/2002 | Tornier | A61F 2/30734 623/22.32 |
| 6,866,685 | B2 | 3/2005 | Chan et al. | |
| 8,398,650 | B1 * | 3/2013 | Burgi | A61F 2/4609 606/99 |
| 10,322,002 | B2 * | 6/2019 | Kazanovicz | A61F 2/36 |
| 2004/0188011 | A1 * | 9/2004 | Jones | A61L 27/446 156/272.8 |
| 2005/0202371 | A1 | 9/2005 | McGuire | |
| 2007/0088442 | A1 | 4/2007 | Cima et al. | |
| 2007/0208428 | A1 * | 9/2007 | Tepic | A61F 2/34 623/22.32 |
| 2009/0088864 | A1 * | 4/2009 | Lewis | A61F 2/34 623/22.21 |
| 2010/0174380 | A1 * | 7/2010 | Lewis | A61F 2/32 623/22.11 |
| 2010/0268348 | A1 * | 10/2010 | Ries | A61F 2/34 623/22.21 |
| 2014/0074249 | A1 * | 3/2014 | Davenport | A61F 2/4609 623/22.24 |
| 2015/0190231 | A1 * | 7/2015 | Hartman | A61F 2/34 623/22.29 |
| 2017/0202671 | A1 * | 7/2017 | Ries | A61F 2/32 |
| 2018/0028320 | A1 | 2/2018 | Forsell | |
| 2018/0168813 | A1 * | 6/2018 | Faccioli | A61F 2/389 |
| 2018/0344466 | A1 | 12/2018 | Lewallen et al. | |
| 2019/0053915 | A1 * | 2/2019 | Macke | A61F 2/34 |
| 2020/0383789 | A1 * | 12/2020 | Magagnoli | A61F 2/30771 |

FOREIGN PATENT DOCUMENTS

| | | |
|---|---|---|
| CN | 108836577 A | 11/2018 |
| WO | 2013120213 A1 | 8/2013 |

* cited by examiner

ARTICULAR FOSSA PROSTHESIS AND ARTICULAR PROSTHESIS WITH ARTICULAR FOSSA PROSTHESIS

CROSS-REFERENCE TO RELATED APPLICATION(S)

The present application claims priority to Chinese Patent Application No. 201910105283.9, filed on Feb. 1, 2019 and entitled "Articular Fossa Prosthesis and Articular Prosthesis with Articular Fossa Prosthesis", the contents of which are hereby incorporated by reference in its entirety.

TECHNICAL FIELD

The disclosure relates to a field of artificial joint implants, and particularly to an articular fossa prosthesis and an articular prosthesis with the articular fossa prosthesis.

BACKGROUND

Total hip joint replacement has been quite popular in the field of artificial joints. However, ceramic or ultra-high molecular weight polyethylene is adopted for most of acetabular lined prostheses in existing products. Hardness of the ceramic and even the polyethylene is far higher than hardware of a human physiological acetabular cartilage tissue, which makes a feeling of a patient walking after rehabilitation quite different from a feeling of a body before an operation. Very few organizations in this industry ever try to use polymer materials (for example, polyurethane, polyvinyl alcohol gel and polylactic acid) with hardware and elasticity approximate to those of a human natural physiological cartilage as an articular friction surface. Wear resistance and mechanical performance may meet requirements. However, since these materials have high deformability, the friction surface subjected to a pressure load is closely attached to an articular prosthesis friction surface (usually ceramic or hard metal) on the opposite side, which makes it impossible for a synovial fluid to keep completely covering a part between the articular friction surfaces and further makes part or even most of the friction surfaces lack of effective lubrication to finally cause rapid wear and failure of the polymer materials.

SUMMARY

The disclosure is intended to provide an articular fossa prosthesis and an articular prosthesis with the articular fossa prosthesis, to solve the problem of premature failure of an artificial joint due to the fact that a friction surface of the artificial joint is lack of effective lubrication and a joint material is worn rapidly in a conventional art.

According to one aspect of the disclosure, an articular fossa prosthesis is provided, which is disposed in a target skeleton and includes an outer cup and a lining, wherein the outer cup is disposed in the target skeleton, the lining is disposed in the outer cup, a first communicating passage communicated with an articular capsule is disposed on the outer cup, an inlet of the first communicating passage is disposed on a surface, exposed into the articular capsule, of the outer cup, and an outlet of the first communicating passage is disposed on the surface, contacting with the lining, of the outer cup; and a second communicating passage communicated with the articular capsule is disposed on the lining, a part of inlets of the second communicating passage are disposed on a surface, exposed into the articular capsule, of the lining, a part of inlets of the second communicating passage are disposed on a surface, contacting with the outer cup, of the lining and communicated with the first communicating passage, outlets of the second communicating passage are disposed on a surface, contacting with an adapted articular head structure, of the lining, and the second communicating passage guides a synovial fluid to a contact surface between the lining and the articular head structure.

In some embodiments, the first communicating passage includes a first tubular passage and a first grooved passage, the first tubular passage is disposed in the outer cup, an inlet of the first tubular passage is disposed on the surface, exposed into the articular capsule, of the outer cup, the first grooved passage is disposed on an inner surface of the outer cup, at least part of outlets of the first tubular passage are disposed in the first grooved passage, the second communicating passage includes a second tubular passage, the second tubular passage is disposed in the lining, inlets of the second tubular passage are disposed on the surface, exposed into the articular capsule, of the lining and the surface, contacting with the outer cup, of the lining, and an outlet of the second tubular passage is disposed on the surface, contacting with the adapted articular head structure, of the lining.

In some embodiments, the first grooved passage includes a first groove, a clamping protruding portion adapted to the first groove is disposed on the lining, and the clamping protruding portion extends into the first groove for clamping fit under a condition that the outer cup and the lining are assembled.

In some embodiments, an overflowing gap is formed between the clamping protruding portion and the first groove to communicate the first communicating passage and the second communicating passage.

In some embodiments, the first grooved passage further includes multiple second grooves, and the multiple second grooves are radially formed in the inner surface of the outer cup and communicated with the first groove.

In some embodiments, an inlet of the second groove is disposed on the surface, exposed into the articular capsule, of the outer cup.

In some embodiments, the second communicating passage further includes a second grooved passage disposed on an outer surface of the lining, the second grooved passage includes a third groove formed in the clamping protruding portion, and a part of inlets of the second communicating passage are disposed on the third groove.

In some embodiments, the second grooved passage further includes a fourth groove, the fourth groove is spaced from the third groove, and a part of inlets of the second communicating passage are disposed on the fourth groove.

In some embodiments, a part of outlets of the second communicating passage disposed on the surface, contacting with the adapted articular head structure, of the lining are provided with accommodation pools, and an opening diameter of each of the accommodation pools is larger than an opening diameter of each of the outlets of the second communicating passage.

In some embodiments, the articular fossa prosthesis is an acetabular prosthesis, and the inlet of the first communicating passage is disposed on an end face of the outer cup.

In some embodiments, the outer cup is made from a ceramic or metallic material, and the lining is made from an elastic polymer material.

In some embodiments, the lining is made from a transparent material, and the second communicating passage is formed by a femtosecond laser engraving technology.

In some embodiments, the outer cup is manufactured by use of a metal and ceramic Three-Dimensional (3D) printing technology to conveniently obtain the first tubular passage with spatial flexibility characteristic, and structures thereof such as the first groove and the second groove may also be machined by the 3D printing technology or post mechanical cutting.

In some embodiments, the outer cup is manufactured by use of a metal and ceramic mold pressing and sintering method to conveniently obtain the first tubular passage with spatial flexibility characteristic, and structures thereof such as the first groove and the second groove may also be machined by mold pressing and sintering or post mechanical cutting.

In some embodiments, the lining is made from a transparent elastic polymer material, and the second communicating passage is formed by the femtosecond laser engraving technology.

According to another aspect of the disclosure, an articular prosthesis is provided, which is disposed between a first skeleton and second skeleton capable of moving relative to each other and includes an articular fossa prosthesis and an articular head prosthesis, wherein the articular fossa prosthesis is disposed on the first skeleton, the articular head prosthesis is disposed on the second skeleton, and the articular fossa prosthesis is the abovementioned articular fossa prosthesis.

With adoption of the technical solutions of the disclosure, the outer cup and the lining are two components respectively, and are combined into the articular fossa prosthesis, so that the outer cup and the lining may be made and formed from different materials respectively, which is favorable for meeting a fixing effect between the outer cup and a skeleton of a patient and reducing wear between the lining and an articular head. The inlet of the first communicating passage on the outer cup is disposed on the surface, exposed into the articular capsule, of the outer cup and connected with the second communicating passage, the inlets of the second communicating passage on the lining are disposed on the surface, exposed into the articular capsule, of the lining, and the synovial fluid in the articular capsule is guided to the contact surface between the lining and the articular head structure, so that the contact surface between the lining and the adapted articular head structure may be fully lubricated, a wear rate of the lining and the articular head structure is reduced, service life of the articular fossa prosthesis is ensured, and an operation frequency of the patient is reduced.

BRIEF DESCRIPTION OF THE DRAWINGS

The drawings forming a part of the application in the specification are adopted to provide a further understanding to the disclosure. Schematic embodiments of the disclosure and descriptions thereof are adopted to explain the disclosure and not intended to form improper limits to the disclosure. In the drawings.

Herein, the drawings include the following drawing reference signs:

10: outer cup; 11: first tubular passage; 12: first groove; 13: second groove; 14: inlet of second groove; 15: inlet of first tubular passage; 16: outlet of first tubular passage; 17: end face of outer cup; 18: outlet of first tubular passage; 20: lining; 21: second tubular passage; 22: clamping protruding portion; 23: third groove; 24: fourth groove; 25: accommodation pool; 26: inlet of second tubular passage; 27: end face of lining; 30: ball head; 40: femoral stem; and 50: femur.

DETAILED DESCRIPTION OF THE EMBODIMENTS

It is to be noted that the embodiments in the application and characteristics in the embodiments may be combined without conflicts. The disclosure will be described below with reference to the drawings and in combination with the embodiments in detail.

Figure 1:
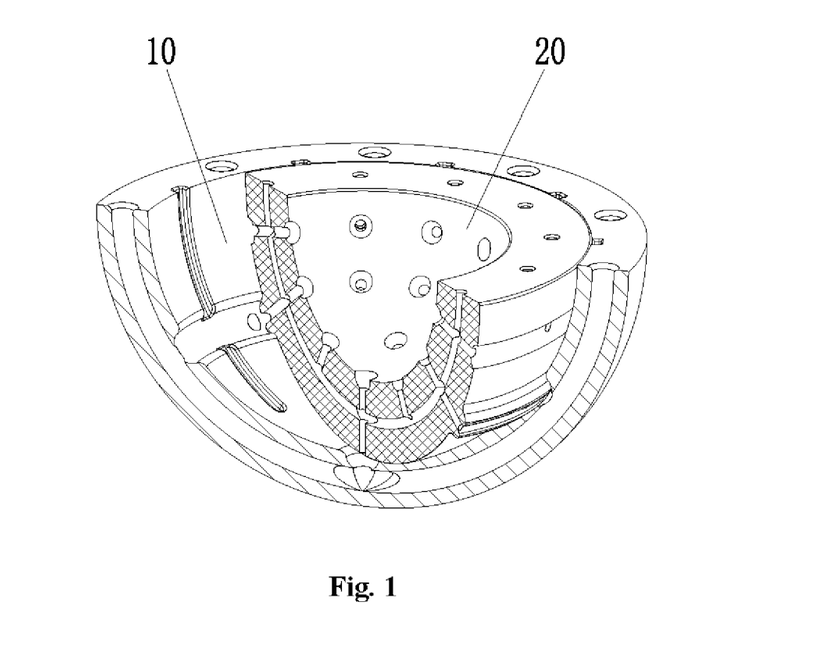
FIG. 1 is a structure diagram of an articular fossa prosthesis according to an embodiment of the disclosure.

An articular fossa prosthesis of the application may be applied to a joint capable of relatively rotating and sliding such as a shoulder joint and a hip joint. In an embodiment, the articular fossa prosthesis is an acetabular prosthesis, and may be disposed in a hip bone to substitute a primary acetabular bone of a patient. Specifically, connective tissues around a joint form a sealed articular cavity of a membranous capsule, and the membranous capsule is called an articular capsule. A synovial membrane in the articular capsule secretes a synovial fluid to reduce friction between connected bones in the joint. As shown in FIG. 1, the articular fossa prosthesis of the embodiment includes an outer cup 10 and a lining 20. The outer cup 10 is disposed in a target skeleton (which may be a hip bone), the lining 20 is disposed in the outer cup 10, and an articular ball head may be movably disposed in the lining 20. A first communicating passage communicated with an articular capsule is disposed on the outer cup 10, an inlet of the first communicating passage is disposed on the surface, exposed into the articular capsule, of the outer cup 10, and an outlet of the first communicating passage is disposed on the surface, contacting with the lining 20, of the outer cup 10. A second communicating passage communicated with the articular capsule is disposed on the lining 20. Herein, a part of inlets of the second communicating passage are disposed on an outer surface, opposite to the outer cup 10, of the lining 20 and communicated with the first communicating passage, a part of inlets of the second communicating passage are disposed on the surface, exposed into the articular capsule, of the lining 20, and outlets of the second communicating passage are disposed on an inner surface, contacting with an adapted articular ball head structure, of the lining 20.

With adoption of the technical solution of the embodiment, the outer cup 10 and the lining 20 are two components respectively, and are combined into the articular fossa prosthesis, so that the outer cup 10 and the lining 20 may be made and formed from different materials respectively, which is favorable for meeting a fixing effect between the outer cup 10 and a skeleton of a patient and reducing wear between the lining 20 and an articular head. The inlet of the first communicating passage on the outer cup 10 is disposed on the surface, exposed into the articular capsule, of the outer cup 10 and connected with the second communicating passage, the inlets of the second communicating passage on the lining 20 are disposed on the surface, exposed into the articular capsule, of the lining 20, and a synovial fluid in the articular capsule is guided to the contact surface between the lining 20 and the articular head structure, so that the contact surface between the lining 20 and the adapted articular head structure may be fully lubricated, a wear rate of the lining 20 and the articular head structure is reduced, service life of the articular fossa prosthesis is ensured, and an revision operation frequency of the patient is reduced.

Preferably, in the embodiment, the outer cup 10 is made from a metallic material by use of a 3D printing technology to ensure hardness of the outer cup 10 and also make it easy to form a structure favorable for fixing the skeleton of the patient such as a porous structure and the first communicating passage with certain spatial flexibility characteristic on an outer surface of the outer cup 10. In another embodiment that is not presented, the outer cup may also be made from a medical material such as ceramic, and may also be machined by technical means of mechanical cutting, mold pressing and sintering and the like.

Preferably, in the embodiment, the lining 20 is made from an elastic polymer material to ensure elasticity thereof, and a medical material such as polyurethane, polyvinyl alcohol gel and polylactic acid may specifically be adopted. Since the second communicating passage is disposed in the lining 20, under the action of a force generated by movement of the patient, the lining 20 may be compressed to be deformed or decompressed to be recovered to act like a pump and pump the synovial fluid into the contact surface or actively suck it into the second communicating passage to improve a lubrication effect between the lining 20 and the ball head. Moreover, such a pump effect may also act on the first communicating passage through deformation of the lining 20 to provide positive and negative pressure for sucking or squeezing the synovial fluid for the first communicating passage to improve the lubrication effect between the outer cup 10 and the lining 20.

More preferably, in the embodiment, the lining 20 is made from a transparent material, and the second communicating passage is formed by a femtosecond laser engraving technology. Some cases in various present tests also try to obtain a porous polymer structure to facilitate storage and delivery of the synovial fluid of the joint, but most of such designs are based on processes such as a lyophilization method, a foaming method and a sintering method, and by these methods, only a random disordered uni-structural porous material may be obtained, it may not be ensured that all pores are through and internal mechanical characteristics may also not be effectively designed and controlled. While for the articular fossa prosthesis of the embodiment, a pre-designed passage may be engraved in the transparent polyurethane material by a femtosecond laser engraving process, cut-through performance of the passage, the mechanical characteristics of the lining and a distribution of the synovial fluid on the contact surface are simultaneously ensured, and the lubrication effect is improved.

Figure 2:
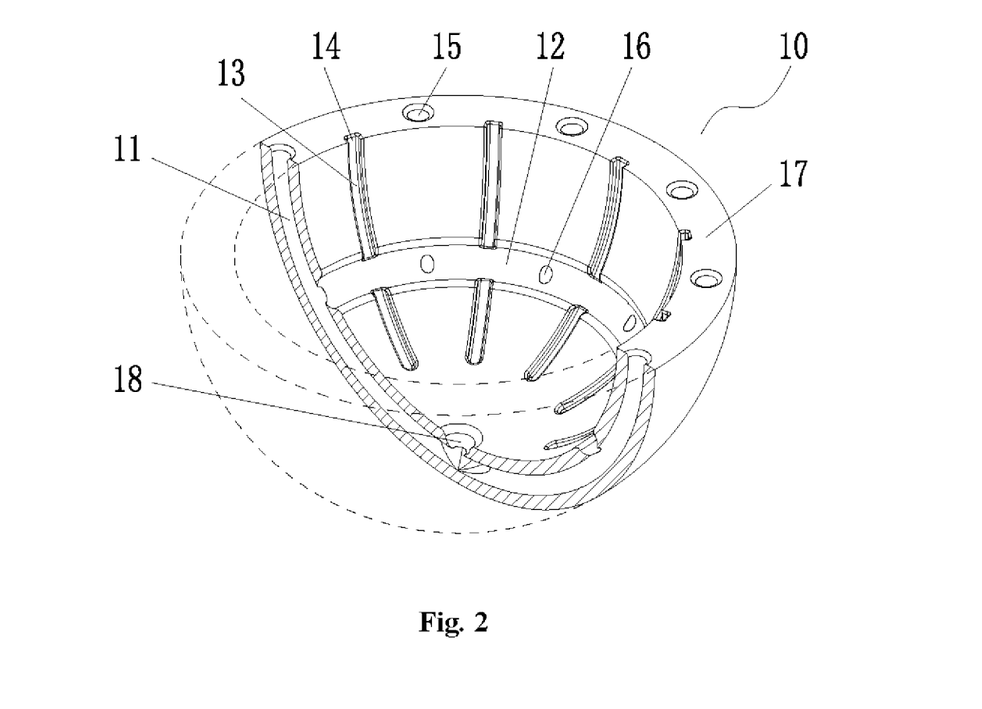
FIG. 2 is a structure diagram of an outer cup of the articular fossa prosthesis in FIG. 1.
Figure 3:
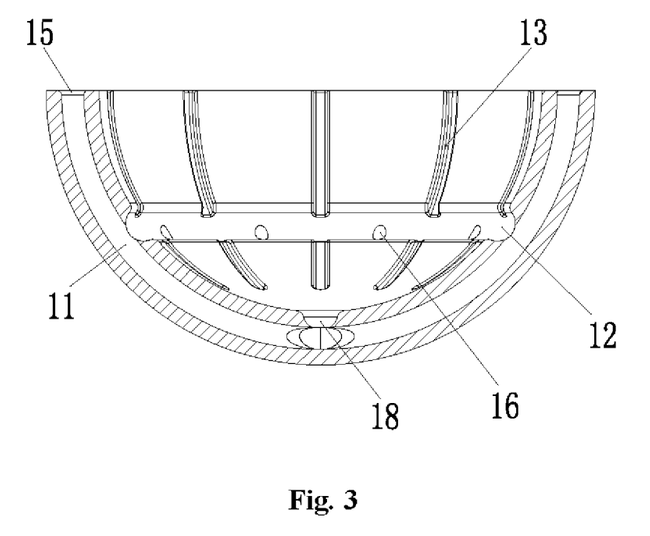
FIG. 3 is a sectional structure diagram of the outer cup in FIG. 2.

As shown in FIG. 2 and FIG. 3, in the embodiment, the first communicating passage includes a first tubular passage 11 and a first grooved passage, and the first tubular passage 11 is disposed in the outer cup 10. After the outer cup 10 is implanted in the patient, the outer surface of the outer cup 10 is covered by a bone bed of the hip bone and the inner surface is covered by the lining 20, so that an inlet 15 of the first tubular passage is disposed on an end face 17 of the outer cup to be exposed into the articular capsule to ensure that the synovial fluid may enter the first tubular passage 11. In the embodiment, a cross section of the first tubular passage 11 is a circle of which a diameter is more than or equal to 0.5 mm. In another embodiment that is not presented, the cross section of the first communicating passage may not be a circle and event not be a regular shape and an equivalent circle diameter thereof should also be more than or equal to 0.5 mm (herein, the equivalent circle diameter refers to a diameter of a circle of which an area is the same as that of the irregular shape).

As shown in FIG. 1 to FIG. 5, the first grooved passage includes a first groove 12, the first groove 12 is annularly disposed on the inner spherical surface of the outer cup 10, multiple outlets 16 of the first tubular passage are disposed at a groove bottom of the first groove 12, and an outlet 18 of the first tubular passage is disposed on the inner spherical surface of the outer cup 10. A clamping protruding portion 22 adapted to the first groove 12 is disposed on the lining 20, and the clamping protruding portion 22 extends into the first groove 12 under the condition that the outer cup 10 and the lining 20 are assembled to mutually lock the outer cup 10 and the lining 20 to prevent the lining 20 from regression and separation.

As shown in FIG. 2 and FIG. 3, in the embodiment, the first grooved passage further includes multiple second grooves 13, and the multiple second grooves 13 are radially formed in the inner surface of the outer cup 10 and communicated with the first groove 12. Inlets 14 of the second grooves are disposed on the end face 17 of the outer cup. The synovial fluid may enter the first tubular passage 11 from the inlet 15 of the first tubular passage and enter the second grooves 13 through the outlets 16 of the first tubular passage and the first groove 12, and may also directly enter the second grooves 13 from the inlets 14 of the second grooves.

Figure 4:
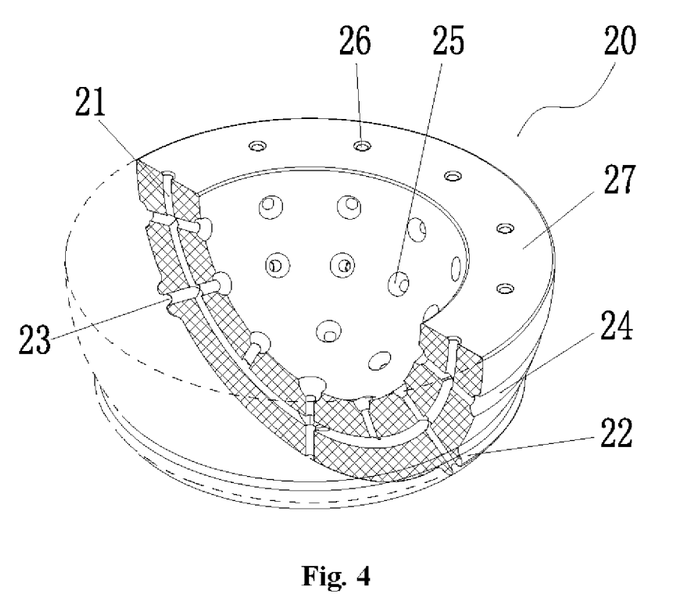
FIG. 4 is a structure diagram of a lining of the articular fossa prosthesis in FIG. 1.
Figure 5:
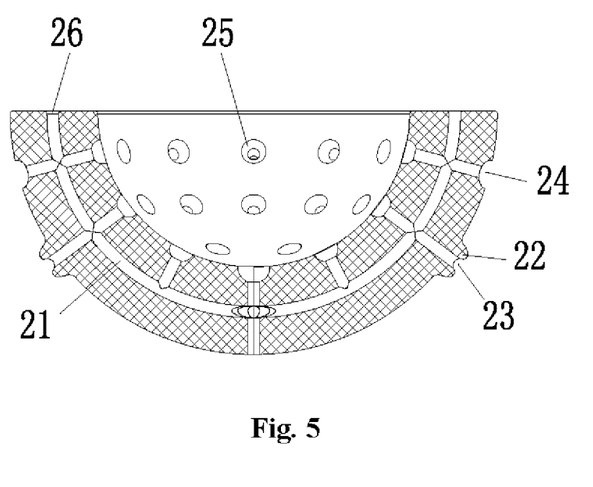
FIG. 5 is a sectional structure diagram of the lining in FIG. 4.

As shown in FIG. 4 and FIG. 5, in the embodiment, the second communicating passage includes a second tubular passage 21, and the second tubular passage 21 is disposed in the lining 20. After the lining 20 is implanted in the patient, the outer surface of the lining 20 is covered by the outer cup 10 and the inner surface is covered by the articular ball head, so that an inlet 26 of the second tubular passage is disposed on an end face 27 of the lining to be exposed into the articular capsule to ensure that the synovial fluid may enter the second tubular passage 21. Outlets of the second tubular passage are disposed on the inner surface, contacting with the adapted articular ball head, of the lining 20.

As shown in FIG. 4 and FIG. 5, inlets of the second communicating passage are also disposed on the surface, contacting with the outer cup 10, of the lining 20 such that the second communicating passage may guide the synovial fluid in the first communicating passage to the contact surface between the lining 20 and the articular ball head. Specifically, the second communicating passage further includes a second grooved channel disposed on the outer surface of the lining 20, the second grooved passage includes a third groove 23 and a fourth groove 24, the third groove 23 is disposed on the clamping protruding portion 22, the fourth groove 24 and the third groove 23 are disposed on the outer surface of the lining 20 at an interval, and the inlets, facing the outer cup 10, of the second communicating passage are disposed at groove bottoms of the third groove 23 and the fourth groove 24. The synovial fluid in the second grooves 13 may enter the second communicating passage through the fourth groove 24 and further coat the contact surface between the lining 20 and the articular ball head. In the embodiment, a cross section of an inlet, facing the outer cup 10, of the lining 20 is a circle of which a diameter is 0.05 mm to 3 mm. In another embodiment that is not presented, the cross section of the inlet, facing the outer cup, of the lining may not be a circle and even not be a regular shape and an equivalent circle diameter thereof should also be 0.05 mm to 3 mm.

For ensuring that the synovial fluid smoothly enters the second communicating passage from the first communicating passage, in the embodiment, an overflowing gap is formed between the clamping protruding portion 22 and the first groove 12, and the synovial fluid enters the overflowing gap through the first tubular passage 11, enters the second communicating passage through an opening of the third groove 23 and further coats the contact surface between the lining 20 and the articular ball head to achieve the lubrication effect.

In the embodiment, accommodation pools 25 are disposed on the inner surface, contacting with the articular ball head, of the lining 20, the accommodation pools 25 are communicated with the outlets, facing the articular ball head, of the second communicating passage, and an opening diameter of each of the accommodation pools 25 is larger than an opening diameter of each of the outlets of the second communicating passage such that the synovial fluid may be stored in the accommodation pools 25. In the embodiment, a cross section of an outlet, facing the ball head, of the lining 20 is a circle of which a diameter of 0.03 mm to 1.5 mm, and an opening of the accommodation pool 25 is a circle of which a diameter is 0.05 mm to 2 mm. In another embodiment that is not presented, the cross section of the outlet, facing the ball head, of the lining may not be a circle and even not be a regular shape and an equivalent circle diameter should also be 0.03 mm to 1.5 mm. An equivalent circle diameter of the opening of each of the accommodation pools should be 0.05 mm to 2 mm.

According to the articular fossa prosthesis of the embodiment, the transparent polymer material with hardness and elasticity parameters approximate to those of a human cartilage is adopted, so that the patient may feel stronger and more comfortable when walking after rehabilitation. In addition, the first communicating passage and second communicating passage for delivering the synovial fluid are disposed on the lining of the acetabular bone and the outer cup of the acetabular bone, so that the articular synovial fluid may be effectively delivered to a friction interface. The polymer lined prosthesis with certain elasticity is cyclically compressed and released under the action of an alternating load of a body weight when the patient walks, and the synovial fluid in the second communicating passage in the lining may be alternately squeezed and sucked, so that the synovial fluid may be continuously delivered to the articular friction interface, and problems about lubrication of the friction interface are solved to ensure that service life of the implanted prosthesis is greatly prolonged.

Figure 6:
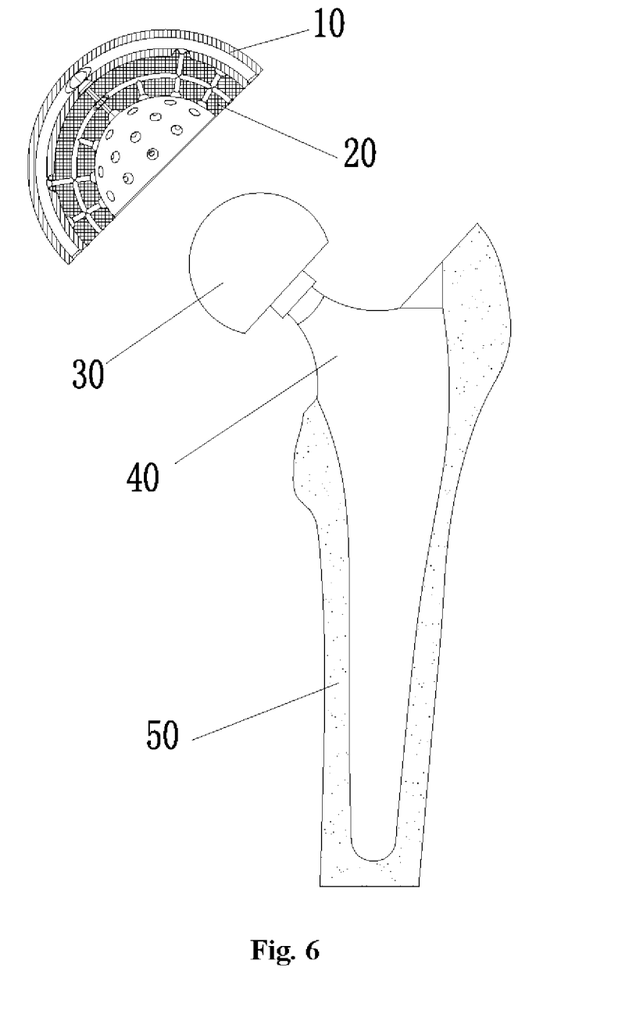
FIG. 6 is a structure diagram of an articular prosthesis according to an embodiment of the disclosure.

The application also provides an articular prosthesis. The articular prosthesis of the embodiment is a hip joint prosthesis and may be disposed between a femur and a hip bone. As shown in FIG. 6, the articular prosthesis of the embodiment includes an articular fossa prosthesis and an articular head prosthesis, the articular fossa prosthesis is disposed on the hip bone and the articular head prosthesis is disposed on the femur. The articular fossa prosthesis is an articular fossa prosthesis including part or all of the abovementioned technical features and specifically includes an outer cup 10 and a lining 20, and the articular head prosthesis includes a ball head 30 and a femoral stem 40. The femoral stem 40 may be implanted into the femur 50 of a patient. The articular prosthesis of the embodiment has the advantages of complete lubrication, low wear rate and long service life.

From the above description, it can be seen that the abovementioned embodiments of the disclosure have the following technical effects.

The outer cup and the lining are two components respectively, and are combined into the articular fossa prosthesis, so that the outer cup and the lining may be made and formed from different materials respectively, which is favorable for meeting a fixing effect between the outer cup and a skeleton of a patient and reducing wear between the lining and an articular head. The inlet of the first communicating passage on the outer cup is disposed on the surface, exposed into the articular capsule, of the outer cup and connected with the second communicating passage, the inlets of the second communicating passage on the lining are disposed on the surface, exposed into the articular capsule, of the lining, and the synovial fluid in the articular capsule is guided to the contact surface between the lining and the articular head structure, so that the contact surface between the lining and the adapted articular head structure may be fully lubricated, a wear rate of the lining and the articular head structure is reduced, service life of the articular fossa prosthesis is ensured, and a revision operation frequency of the patient is reduced.

The above is only the preferred embodiment of the disclosure and not intended to limit the disclosure. For those skilled in the art, the disclosure may have various modifications and variations. Any modifications, equivalent replacements, improvements and the like made within the spirit and principle of the disclosure shall fall within the scope of protection of the disclosure.

What is claimed is:

1. An articular fossa prosthesis, disposed in a target skeleton and comprising an outer cup and a lining, wherein the outer cup is disposed in the target skeleton, the lining is disposed in the outer cup, a first communicating passage communicated with an articular capsule is disposed on the outer cup, inlets of the first communicating passage are disposed on a surface, exposed into the articular capsule, of the outer cup, and outlets of the first communicating passage are disposed on a surface, contacting with the lining, of the outer cup; and a second communicating passage communicated with the articular capsule is disposed on the lining, the second communicating passage comprises a plurality of inlets and a plurality of outlets, a part of the inlets of the second communicating passage are disposed on a surface, exposed into the articular capsule, of the lining, a part of the inlets of the second communicating passage are disposed on a surface, contacting with the outer cup, of the lining and communicated with the first communicating passage, outlets of the second communicating passage are disposed on a surface, contacting with an adapted articular head prosthesis, of the lining, and the second communicating passage guides a synovial fluid to a contact surface between the lining and the articular head prosthesis;

the first communicating passage comprises a first tubular passage and a first grooved passage, the first tubular passage is disposed in the outer cup, inlets of the first tubular passage are disposed on the surface, exposed into the articular capsule, of the outer cup, the first grooved passage is disposed on an inner surface of the outer cup, the first tubular passage comprises a plurality of outlets, at least part of the outlets of the first tubular passage are disposed in the first grooved passage, the second communicating passage comprises a second tubular passage, the second tubular passage is disposed in the lining, inlets of the second tubular passage are disposed on the surface, exposed into the articular capsule, of the lining and the surface, contacting with the outer cup, of the lining, and outlets of the second tubular passage are disposed on the surface, contacting with the adapted articular head prosthesis, of the lining.

2. The articular fossa prosthesis as claimed in claim 1, wherein the first grooved passage comprises a first groove, a clamping protruding portion adapted to the first groove is disposed on the lining, and the clamping protruding portion extends into the first groove for clamping fit under a condition that the outer cup and the lining are assembled.

3. The articular fossa prosthesis as claimed in claim 2, wherein an overflowing gap is formed between the clamping protruding portion and the first groove to communicate the first communicating passage and the second communicating passage.

4. The articular fossa prosthesis as claimed in claim 2, wherein the first grooved passage further comprises a plurality of second grooves, and the plurality of second grooves are radially formed in the inner surface of the outer cup and communicated with the first groove.

5. The articular fossa prosthesis as claimed in claim 4, wherein inlets of the second grooves are disposed on the surface, exposed into the articular capsule, of the outer cup.

6. The articular fossa prosthesis as claimed in claim 2, wherein the second communicating passage further comprises a second grooved passage disposed on an outer surface of the lining, the second grooved passage comprises a third groove formed in the clamping protruding portion, and a part of the inlets of the second communicating passage are disposed on the third groove.

7. The articular fossa prosthesis as claimed in claim 6, wherein the second grooved passage further comprises a fourth groove, the fourth groove is spaced from the third groove, and a part of the inlets of the second communicating passage are disposed on the fourth groove.

8. The articular fossa prosthesis as claimed in claim 1, wherein a part of the outlets of the second communicating passage disposed on the surface, contacting with the adapted articular head prosthesis, of the lining are provided with accommodation pools, and an opening diameter of each of the accommodation pools is larger than an opening diameter of each of the outlets of the second communicating passage.

9. The articular fossa prosthesis as claimed in claim 1, wherein the articular fossa prosthesis is an acetabular prosthesis, and the inlets of the first communicating passage are disposed on an end face of the outer cup.

10. The articular fossa prosthesis as claimed in claim 1, wherein the outer cup is made from a ceramic or metallic material, and the lining is made from an elastic polymer material.

11. The articular fossa prosthesis as claimed in claim 1, wherein the lining is made from a transparent material, and the second communicating passage is formed by a femtosecond laser engraving technology.

12. An articular prosthesis, disposed between a first skeleton and second skeleton capable of moving relative to each other and comprising the articular fossa prosthesis as claimed in claim 1 and the articular head prosthesis, wherein the articular fossa prosthesis is disposed on the first skeleton, the articular head prosthesis is disposed on the second skeleton.

13. The articular prosthesis as claimed in claim 12, wherein the first communicating passage comprises a first tubular passage and a first grooved passage, the first tubular passage is disposed in the outer cup, inlets of the first tubular passage are disposed on the surface, exposed into the articular capsule, of the outer cup, the first grooved passage is disposed on an inner surface of the outer cup, the first tubular passage comprises a plurality of outlets, at least part of the outlets of the first tubular passage are disposed in the first grooved passage, the second communicating passage comprises a second tubular passage, the second tubular passage is disposed in the lining, inlets of the second tubular passage are disposed on the surface, exposed into the articular capsule, of the lining and the surface, contacting with the outer cup, of the lining, and outlets of the second tubular passage are disposed on the surface, contacting with the articular head prosthesis, of the lining.

14. The articular prosthesis as claimed in claim 13, wherein the first grooved passage comprises a first groove, a clamping protruding portion adapted to the first groove is disposed on the lining, and the clamping protruding portion extends into the first groove for clamping fit under a condition that the outer cup and the lining are assembled.

15. The articular prosthesis as claimed in claim 14, wherein an overflowing gap is formed between the clamping protruding portion and the first groove to communicate the first communicating passage and the second communicating passage.

16. The articular prosthesis as claimed in claim 14, wherein the first grooved passage further comprises a plurality of second grooves, and the plurality of second grooves are radially formed in the inner surface of the outer cup and communicated with the first groove.

17. The articular prosthesis as claimed, in claim 16, wherein inlets of the second grooves are disposed on the surface, exposed into the articular capsule, of the outer cup.

18. The articular prosthesis as claimed in claim 14, wherein the second communicating passage further comprises a second grooved passage disposed on an outer surface of the lining, the second grooved passage comprises a third groove formed in the clamping protruding portion, and a part of the inlets of the second communicating passage are disposed on the third groove.

19. The articular prosthesis as claimed in claim 18, wherein the second grooved passage further comprises a fourth groove, the fourth groove is spaced from the third groove, and a part of the inlets of the second communicating passage are disposed on the fourth groove.

* * * * *